United States Patent [19]

Shepherd

[11] Patent Number: 4,463,177

[45] Date of Patent: Jul. 31, 1984

[54] PROCESS FOR MAKING M-HYDROXYPHENYL SUBSTITUTED COMPOUNDS

[75] Inventor: Robin G. Shepherd, Maidenhead, England

[73] Assignee: John Wyeth & Brother Limited, Maidenhead, England

[21] Appl. No.: 444,653

[22] Filed: Nov. 26, 1982

[30] Foreign Application Priority Data

Dec. 2, 1981 [GB] United Kingdom ............... 8136364
Jul. 16, 1982 [GB] United Kingdom ............... 8220721

[51] Int. Cl.$^3$ .......................................... C07D 211/74
[52] U.S. Cl. .................... 546/221; 546/216; 546/243; 546/237; 548/551; 548/571; 548/544; 260/239 B; 260/239.3 R; 260/239.3 B; 549/346; 549/416; 549/414; 549/475; 549/424; 549/9; 549/28; 549/13; 549/62; 549/29
[58] Field of Search ............ 546/216, 243, 221, 237; 548/551, 571, 544; 260/239.3 R, 239 B; 549/346, 416, 414, 475, 429, 9, 28, 13

[56] References Cited

U.S. PATENT DOCUMENTS

2,197,241  4/1980  Cavalla et al. ............... 260/239.3 R
4,197,239  4/1980  Cavalla et al. ............... 260/239.3 R

FOREIGN PATENT DOCUMENTS

850777   7/1977  Belgium ...................... 260/239 B
1285025  8/1972  United Kingdom ............ 260/239 B

OTHER PUBLICATIONS

Cavalla et al., "J. Med. Chem.", vol. 8, pp. 316–326 (1965).
Kugita et al., "J. Med. Chem.", vol. 8, pp. 313–316 (1965).

*Primary Examiner*—Robert T. Bond

*Attorney, Agent, or Firm*—Arthur G. Seifert

[57] ABSTRACT m-Hydroxyphenyl substituted compounds of formula

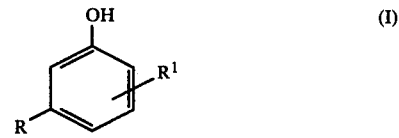

(I)

where R is an organic radical and $R^1$ is hydroen or an organic radical are prepared by dehydrohalogenating a compound of formula

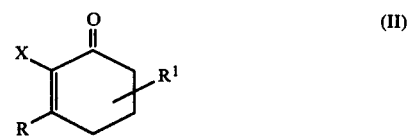

(II)

(where X is chlorine or bromine, and R and $R^1$ have the above meanings). Preferred novel starting materials of formula (II) are of the formula

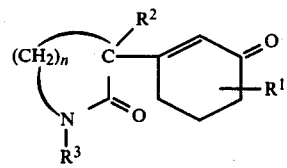

(where $R^1$ and X are as above, n is 2,3 or 4, $R^2$ is hydrogen or lower alkyl and $R^3$ is hydrogen, lower alkyl, lower alkenyl, lower alkynyl, cycloalkyl(lower)alkyl or aryl(lower)alkyl).

15 Claims, No Drawings

PROCESS FOR MAKING M-HYDROXYPHENYL SUBSTITUTED COMPOUNDS

This invention relates to m-hydroxyphenyl substituted compounds, to their preparation and to intermediates used in their preparation.

Many m-hydroxyphenyl substituted compounds are known and are useful particularly as pharmaceuticals. For example analgesic 3-hydroxyphenyl-hexahydroazepines such as meptazinol are disclosed in U.K. Patent Specification No. 1,285,025. Profadol and related pyrrolidines are described in J. Med. Chem. 1965, 8, 316 and Belgian Patent Specification No. 850,777 while myfadol and related piperidines are described in J. Med. Chem., 1965, 8, 313. We have now found a novel process for preparing m-hydroxyphenyl substituted compounds. The process can be used in the preparation of pharmacologically active compounds such as those mentioned above.

According to the invention there is provided a process for preparing m-hydroxyphenyl substituted compounds of the general formula

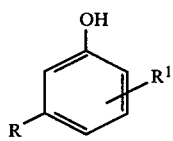

where R is an organic radical and $R^1$ is hydrogen or an organic radical, which process comprises dehydrohalogenating a compound of the general formula

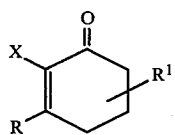

(where R is an organic radical, $R^1$ is hydrogen or an organic radical and X is chlorine or bromine) in the presence of a strong nucleophilic acid catalyst.

The organic radical R, and also $R^1$ when it is an organic radical, may be an aliphatic, aromatic or heterocyclic radical. The radicals may contain substituents, including functional groups. Some substituents may be modified under the conditions of the reaction so that the organic radical R or $R^1$ in the starting material may be different from the organic radical R or $R^1$ in the product.

Preferably $R^1$ is hydrogen. When R is a heterocyclic radical it can be, for example, a monocyclic or bicyclic heterocyclic radical containing one or more hetero atoms. The hetero atom or atoms may be, for example, oxygen, sulphur or nitrogen. Examples of heterocyclic radicals include pyrrolidine, piperidine and hexahydroazepine radicals, particularly those of the formula (III)

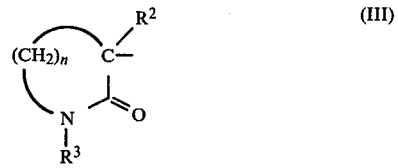

where n is 2,3 or 4 (preferably 4), $R^2$ is hydrogen or lower alkyl and $R^3$ is hydrogen, lower alkyl, lower alkenyl, lower alkynyl, cycloalkyl(lower)alkyl or aryl(lower)alkyl. The term "lower" as used herein means that the radical referred to contains 1 to 6 carbon atoms. The radical preferably contains 1 to 4 carbon atoms. For example, a lower alkyl radical is preferably methyl, ethyl, propyl or butyl. Examples of lower alkenyl and lower alkynyl radicals are allyl, propargyl, 3,3-dimethylallyl and 1-methyl-2-propynyl. An example of cycloalkyl(lower)alkyl is cyclopropylmethyl. Examples of aryl(lower)alkyl are phenethyl or benzyl in which the phenyl group may be substituted by one or more substituents such as halogen, alkoxy, trifluoromethyl or other substituents common in medicinal chemistry.

Compounds of general formula II in which X has the meaning given above, $R^1$ has the meaning given above (preferably hydrogen) and the radical R has formula (III) are novel compounds and are provided by the invention.

The compound of formula (I) in which $R^1$ is hydrogen and R has the formula (III) (where $R^2$ is lower alkyl and and $R^3$ and n are as defined above) may be reduced e.g. with a hydride transfer agent, such as lithium aluminium hydride to a compound of formula (IV)

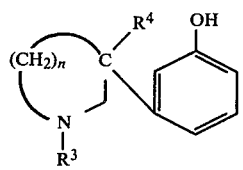

(where $R^4$ is lower alkyl and n and $R^3$ have the meanings given above). The compounds of general formula (IV) are useful as analgesics or as intermediates therefor as explained, for example, in the above mentioned references. The compound of general formula (IV) in which $R^3$ is methyl, n is 4 and $R^4$ is ethyl is the analgesic, meptazinol. Compounds of formula I in which R has the formula (III) where $R^2$ is hydrogen may be C-alkylated to give corresponding compounds in which $R^2$ is lower alkyl. Compounds of formula I or of formula (IV) in which $R^3$ is hydrogen may be N-alkylated to give compounds in which $R^3$ is lower alkyl, lower alkenyl, lower alkynyl, cycloalkyl(lower)alkyl or aryl(lower)alkyl. The reduction, C-alkylation and N-alkylation processes are further described in, for example, U.K. Patent Specification No. 1,285,025 and European patent application No. 0,003,253.

The process of the invention may also be used, for example, in the preparation of compounds of formula (I) in which R is a carboxymethyl radical or a derivative therefor such as —CH$_2$COO(lower)alkyl and $R^1$ is (lower)alkyl, phenyl or substituted phenyl such as chlorophenyl (the substituent $R^1$ being meta to both the R group and the hydroxy group). Such compounds have anti-inflammatory activity or are useful as intermediates for anti-inflammatory compounds as disclosed by Tamura et al, J. Med. Chem. 1977, 20, 709-714.

The process of the invention may also be used in the preparation of a compound of formula (I) in which $R^1$ is hydrogen and R is

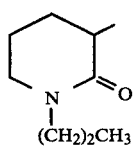
(V)

i.e. a m-hydroxyphenyl substituted compound of formula formula

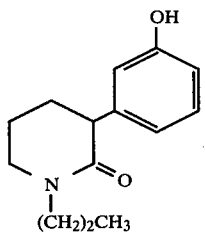
(VI)

The compound is prepared by dehydrohalogenating a compound of general formula

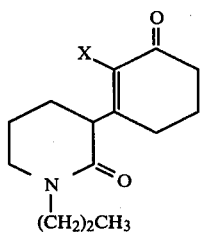
(VII)

where X is chlorine or bromine (preferably bromine) by the process of the invention.

The product of general formula (VI) may be reduced with, for example, a hydride transfer agent (preferably borane-tetrahydrofuran complex) to give a 3-(1-propyl-3-piperidinyl)phenol of formula

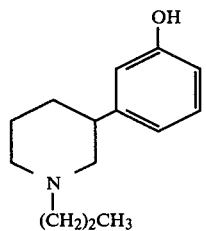
(VIII)

The compound of general formula (VIII) and its pharmaceutically acceptable acid addition salts are known and stated to be selective dopamine autoreceptor agonists which can be used e.g. for the treatment of disease states associated with disturbances in central dopamine autoreceptor transmission.

The process of the invention may be carried out in a solvent such as methylene chloride, chloroform or acetic acid, e.g. under substantially anhydrous conditions. The reaction may be carried out at ambient temperatures. The strong nucleophilic acid catalyst may be for example, hydrogen bromide or hydrogen chloride.

The process has advantages over conventional processes of aromatisation since the starting materials are normally easily isolated, the process employs mild conditions and the process avoids the use of bromine which is difficult to handle on a large scale and which tends to result in overbrominated products.

The starting material, of formula (II) may be prepared by reacting a 2-halocyclohexenone derivative of general formula (IX)

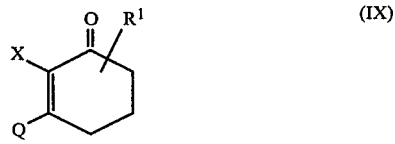
(IX)

where X and $R^1$ are as defined above and Q is a hydrolysable protecting group such as lower alkoxy, benzyloxy or trialkyl-, triaryl- or triaralkyl-siloxy (e.g. trimethyl-silyloxy) with a nucleophilic reagent and subjecting the product to hydrolysis. For example, where R in formula (II) is a radical of formula (III) the nucleophilic reagent may be an anion or dianion of a lactam of general formula (X)

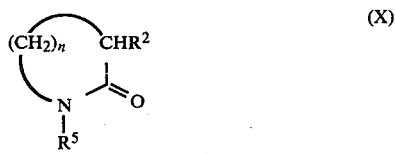
(X)

(where n and $R^2$ are as defined above and $R^5$ is hydrogen, lower alkyl, aryllower alkyl, or trialkyl-, triaryl or triaralkyl-silyl). The preparation and reactions of the anion or dianion of the lactam of formula (VI) is described in, for example, European patent application No. 003,253. When R is formula (II) has the formula (V), the nucleophilic reagent may be an anion (preferably the sodium, potassium, lithium or MgHal anion) of a lactam of general formula (XI)

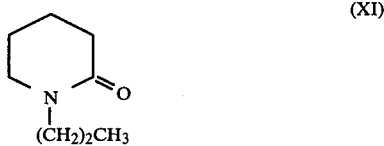
(XI)

The anion of the lactam may be prepared by reacting the lactam with e.g. lithium diisopropylamide.

The 2-halocyclohexanone derivatives of general formula (IX) are known or can be prepared by the process illustrated below

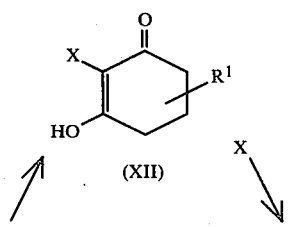
(XII)

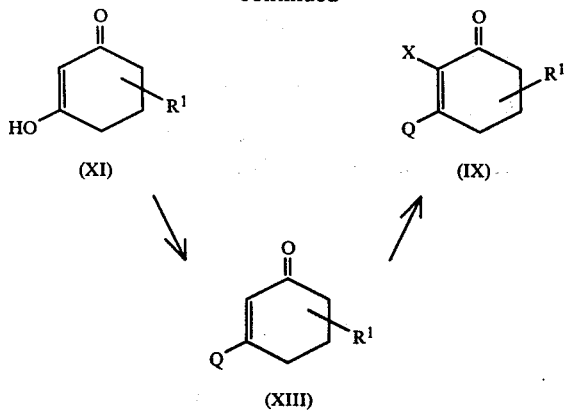

The halogenation step (XI) to (XII) may be carried out by methods known in the art (by reaction with, e.g. N-bromosuccinimide or N-chlorosuccinimide in a solvent such as carbon tetrachloride, with sulphuryl chloride in a solvent such as chloroform or with chlorine or bromine). However, for superior yields, we prefer to brominate using aqueous potassium bromate in aqueous hydrobromic acid or to chlorinate with an aqueous solution of Chloramine T (N-chloro-4-methylbenzenesulphonamide sodium salt).

The halogenation step (XIII) to (IX) may also be carried out by methods known in the art. Preferably in this step X is bromine and the bromination may be carried out, e.g. with bromine in, for example, sodium acetate/acetic acid or with N-bromosuccinimide in, for example, carbon tetrachloride. However, preferably the bromination is effected with N-bromosuccinimide in a more polar solvent such as dichloroethane or acetonitrile.

The steps (XI) to (XIII) and (XII) to (IX) may be carried out by methods known in the art, for example (XI) or (XII) may be reacted with an alcohol in a solvent such as toluene in the presence of an acid with azeotropic removal of water. An alternative method of alkylation is described and claimed in our copending U.K. application filed concurrently herewith which claims priority from U.K. patent application Nos. 8,136,364 and 8,211,201 and which has the title "3-Alkoxycycloalk-2-en-1-ones" (our ref H-312/317). Reaction of compounds (XII) or (XIII) with silylating agents (such as trimethylsilyl chloride in the presence of an organic base) gives compounds in which Q is trialkyl-, triaryl- or triaralkyl-silyloxy.

The following Examples illustrate the invention:

EXAMPLE 1

3-(2-Chloro-3-oxocyclohex-1-enyl)-hexahydro-1-methylazepin-2-one

Lithium disiopropylamide was prepared from n-butyllithium (1.55M in hexane, 6.45 ml) and diisopropylamine (1.4 ml) in tetrahydrofuran (10 ml). It was treated at 0° C. with 1-methylcaprolactam (1.27 g) and then with 2-chloro-3-methoxycyclohexenone (1.61 g) in THF (5 ml). The reaction mixture was stirred for 5 minutes and then poured on to cold 2N hydrochloric acid. After ½ hour toluene was added and the layers separated. The organic phase was washed with aqueous NaOH and water, dried and evaporated to give the crystalline product (1.9 g) m.p. 118°-120° C. (Found: C, 61.4; H, 7.3; N, 5.3%. $C_{13}H_{18}ClNO_2$ requires C, 61.1; H, 7.1; N, 5.5%).

EXAMPLE 2

3-(2-Bromo-3-oxocyclohex-1-enyl)-hexahydro-1-methylazepin-2-one

Lithium diisopropylamide was made from n-butyl lithium (1.55M in hexane, 12.9 ml) and diisopropylamine (2.8 ml) in THF (13 ml). The mixture was treated with 1-methyl-caprolactam (2.54 g) and then with 2-bromo-3-methoxycyclohexenone (4.1 g) in THF (15 ml). After 1 min. the reaction mixture was poured onto 5N HCl (8 ml) and cold water (100 ml). After 0.5 h ether was added and the organic phase separated, dried and evaporated. Recrystallisation of the residue from ethyl acetate gave the title compound (4.9 g), m.p. 112°-115° C. (d). (Found: C, 51.7; H, 6.2; N, 4.7%. $C_{13}H_{18}BrNO_2$ requires: C, 52.0; H, 6.0; 4.7%).

EXAMPLE 3

Following the procedures of Examples 1 and 2 but using the appropriate halomagnesium anion of 3-ethyl-1-methylhexahydroazepin-2-one, the following compounds were prepared:

(a) 3-(2-bromo-3-oxocyclohex-1-enyl)-3-ethyl-hexahydro-1-methylazepin-2-one, m.p. 106°-7° C. (Found: C, 54.7; H, 6.8; N, 4.2%. $C_{15}H_{22}BrNO_2$ requires: C, 54.9; H, 6.8; N, 4.3%)

(b) 3-(2-chloro-3-oxocyclohex-1-enyl)-3-ethylhexahydro-1-methylazepin-2-one, m.p. 115°-116° C. (Found: C, 63.7; H, 7.9; N, 4.85%. $C_{15}H_{22}ClNO_2$ requires C, 63.5; H, 7.8; N, 4.9%).

EXAMPLE 4

Hexahydro-3-(3-hydroxyphenyl)-1-methyl-2H-azepine-2-one (a) 3-(2-Bromo-3-oxocyclohex-1-enyl)-hexahydro-1-methylazepin-2-one (1.48 g) in methylene chloride (10 ml) was treated with 48% HBr in acetic acid. After 3 hours water was added and the organic solvent removed under reduced pressure. The product (844 mg) crystallised from the aqueous solution, m.p. 190°-192° C., identical with authentic material.

(b) A solution of 3-(2-bromo-3-oxocyclohex-1-enyl)-hexahydro-1-methylazepin-2-one (6 g) in chloroform (60 ml) was treated with 48% HBr in acetic acid (1 ml). After 4 hours, NMR indicated completion. Aqueous ammonia was added and the organic solvent removed under reduced pressure to yeild the title compound as a crystalline solid, m.p. 192°-3° (EtOAc).

EXAMPLE 5

Hexahydro-3-(3-hydroxyphenyl)-1-methyl-2H-azepin-2-one (a) Using chloroform as solvent. A solution of 3-(2-chloro-3-oxocyclohex-1-enyl)-hexahydro-1-methylazepin-2-one (5.12 g) in chloroform (50 ml) was treated with 48% HBr in acetic acid (2 ml). After 12 hours the organic solvent was removed under reduced pressure and the residue triturated with aqueous ammonia to yield the title compound m.p. 192°-3° C. (EtOAc).

(b) Using acetic acid as solvent. A solution of 3-(2-chloro-3-oxocyclohex-1-enyl)-hexahydro-1-methylazepin-2-one (5.12 g) in glacial acetic acid (50 ml) was treated with 48% HBr in acetic acid (2 ml). After 12 hours the reaction mixture was poured on to water and the resulting precipitate removed by filtration to yield the title compound m.p. 192°–3° C. (EtOAc).

EXAMPLE 6

Hexahydro-3-ethyl-3-(3-hydroxyphenyl)-1-methyl-2H-azepin-2-one

A solution of 3-(2-bromo-3-oxocyclohex-1-enyl)-3-ethylhexahydro-1-methylazepin-2-one (6.57 g) in dichloromethane (70 ml) was treated with 48% HBr in acetic acid (1 ml). After 3 hours NMR indicated completion. The solvent was removed under reduced pressure and the residue triturated with aqueous ammonia to yield the title compound as a white crystalline solid, m.p. 178°–80° C. (EtOAc).

EXAMPLE 7

Hexahydro-3-ethyl-3-(3-hydroxyphenyl)-1-methyl-2H-azepin-2-one

A solution of 3-(2-chloro-3-oxocyclohex-1-enyl)-3-ethyl-hexahydro-1-methylazepin-2-one (5.68 g) in dichloromethane (60 ml) was treated with 48% HBr in acetic acid (2 ml). After 12 hours the mixture was treated with excess aqueous ammonia, the organic solvent removed under reduced pressure and the resulting solid removed by filtration to give the title compound, m.p. 178°–80° C. (EtOAc).

EXAMPLE 8

3-(2-Bromo-3-oxocyclohex-1-enyl)-1-propyl-2-piperidone

A solution of 1-propyl-2-piperidone (50 mM) in benzene (40 ml) was added dropwise to a solution of lithium di-isopropylamide [ex n-butyl lithium in hexane (32.3 ml, 50 mM), di-isopropylamine (7 ml, 50 mM) and THF (33 ml)]. A solution of 2-bromo-3-methoxycyclohex-2-en-1-one (10.25 g, 50 mM) in THF (40 ml) was added, and after 5 minutes the mixture was quenched by pouring on to excess aqueous hydrochloric acid. Ether extraction followed by passage through a short silica pad using ethyl acetate as eluant gave the title compound as a colourless oil (10.75 g).

EXAMPLE 9

3-(3-Hydroxyphenyl)-1-propyl-2-piperidone

The product of Example 8 (10.5 g, 33.4 mM) in dichloromethane (70 ml) was treated with 48% hydrogen bromide in acetic acid (ca 0.5 ml). After 16 h the solvent was evaporated under reduced pressure and the residue was partitioned between chloroform and water. The organic phase was dried and evaporated and the residue was chromatographed on alumina (neutral, grade 3) using 4% methanol in chloroform as eluant. The appropriate fractions were avaporated and recrystallised from ether to yield the title compound (6.8 g) m.p. 61°–3° (Found: C, 71.9; H, 7.8; 5.6% $C_{14}H_{19}NO_2$ requires C, 72.1; H, 8.2; 6.0%).

EXAMPLE 10

3-(1-Propyl-3-piperidinyl)phenol

The product of Example 9 (4.87 g, 21 mM) in THF (50 ml) was treated with borane—THF (63 ml, 63 mM). After 3 h the mixture was poured on to water and the THF evaporated under reduced pressure. The residue was acidified with 2N hydrochloric acid and the resulting solid removed by filtration. The filtrate was basified (pH 10) and extracted with chloroform and the organic phase was dried and evaporated. The resulting oil was converted to the hydrobromide salt (3.0 g) m.p. 144°–5° (Found: C, 55.1; H, 7.3; N, 4.6% $C_{14}H_{21}NO.\frac{1}{4}H_2O$ requires: C, 55.2; H, 7.3; N, 4.6%).

I claim:

1. A process for preparing a m-hydroxyphenyl substituted compound of the formula:

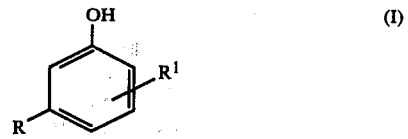

where R is —$CH_2COOH$; —$CH_2COOC_{1-4}$ alkyl; a heterocyclic group of the formula:

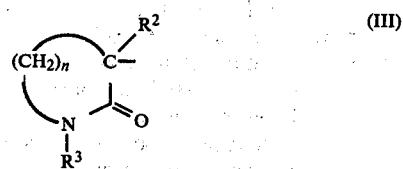

where n is 2, 3 or 4; $R^2$ is hydrogen or $C_{1-6}$ alkyl; and $R^3$ is hydrogen, $C_{1-6}$ alkyl, $C_{1-6}$ alkenyl, $C_{1-6}$ alkynyl, cycloalkyl(lower)alkyl in which the cycloalkyl group contains 3–6 carbon atoms and the (lower)alkyl group contains 1–4 carbon atoms, or phenyl(lower)alkyl in which the phenyl group may be substituted by a halogen, $C_{1-4}$ alkoxy, $C_{1-4}$ alkyl or trifluoromethyl group and the (lower)alkyl group contains 1–4 carbon atoms

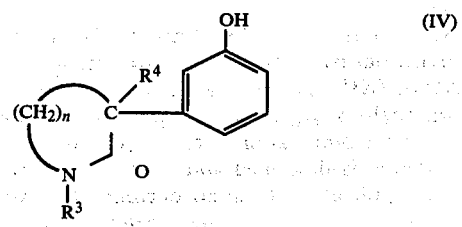

and $R^1$ is hydrogen, $C_{1-6}$ alkyl, phenyl or chlorophenyl (the $R^1$ substituent being meta to both the R group and the hydroxy group), which process comprises dehydrohalogenating a compound of the formula:

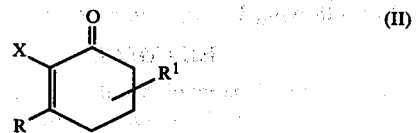

where R and $R^1$ have the meanings given above and X is chlorine or bromine, in the presence of a strong nucleophilic catalyst.

2. A process as claimed in claim 1 wherein $R^1$ is hydrogen.

3. A process as claimed in claim 1 or 2 wherein R is hexahydro-1-methyl-2-oxo-azepine-3-yl, 3-ethyl-hexahydro-1-methyl-2-oxo-azepine-3-yl or 1-propyl-2-oxo-piperid-3-yl.

4. A process as claimed in claim 1 or 2 wherein n is 4.

5. A process as claimed in claims 1, 2, 3, or 4 in which the nucleophilic acid catalyst is hydrogen bromide or hydrogen chloride.

6. A process for preparing m-hydroxyphenyl substituted compound of the general formula:

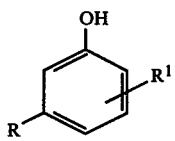

where R is —CH$_2$COOH; —CH$_2$COOC$_{1-4}$ alkyl; a saturated monocyclic heterocyclic group containing 5-7 atoms in the heterocyclic ring, one nitrogen, oxygen or sulfur heteroatom and being optionally substituted on such nitrogen heteroatom with a C$_{1-6}$ alkyl, C$_{1-6}$ alkenyl, C$_{1-6}$ alkynyl, cycloalkyl(lower)alkyl in which the cycloalkyl group contains 3-6 carbon atoms and the lower alkyl group contains 1-6 carbon atoms, or phenyl(lower)alkyl in which the phenyl group may be substituted by a halogen, C$_{1-6}$ alkyl, C$_{1-6}$ alkoxy or trifluoromethyl methyl group and the lower alkyl group contains 1-6 carbon atoms and further being optionally substituted at the three position with a C$_{1-6}$ alkyl group and further being substituted at the two position with a double-bonded oxygen atom; and R$^1$ is hydrogen, C$_{1-6}$ alkyl, phenyl, or phenyl substituted by a chloro, C$_{1-4}$ alkyl, C$_{1-4}$ alkoxy, or trifluoromethyl group, (the R$^1$ substituent being meta to both the R group and the hydroxy group), which process comprises dehydrohalogenating a compound of the general formula:

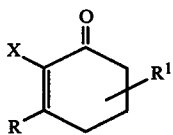

where R and R$^1$ have the meanings given above and X is chlorine or bromine, in the presence of a strong nucleophilic catalyst.

7. A process as claimed in claim 6 wherein R$^1$ is hydrogen.

8. A process as claimed in claim 6 wherein the nucleophilic catalyst is hydrogen bromide or hydrogen chloride.

9. 3-(2-Chloro-3-oxocyclohex-1-enyl)-hexahydro-1-methylazepin-2-one or 3-(2-bromo-3-oxocyclohex-1-enyl)-hexahydro-1-methylazepin-2-one or 3-(2-bromo-3-oxocyclohex-1-enyl)-3-ethyl-hexahydro-1-methylazepin-2-one or 3-(2-chloro-3-oxocyclohex-1-enyl)-3-ethyl-hexahydro-1-methylazepin-2-one.

10. 3-(2-Bromo-3-oxocyclohex-1-enyl)-1-propyl-2-piperidone.

11. A compound of the formula:

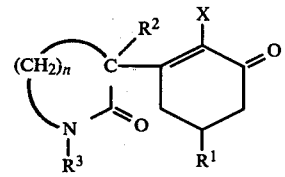

wherein
n is 2, 3 or 4,
X is chlorine or bromine,
R$^1$ is hydrogen, C$_{1-6}$ alkyl, phenyl or chlorophenyl,
R$^2$ is hydrogen or C$_{1-6}$ alkyl,
R$^3$ is hydrogen, C$_{1-6}$ alkyl, C$_{1-6}$ alkenyl, C$_{1-6}$ alkynyl, cycloalkyl(lower)alkyl in which the cycloalkyl group contains from 3-6 carbon atoms and the (lower)alkyl group contains 1-4 carbon atoms, or phenyl(lower)alkyl in which the phenyl group may be substituted by a halogen, C$_{1-4}$ alkoxy, C$_{1-4}$ alkyl, or trifluoromethyl group and (lower)alkyl contains 1-4 carbon atoms.

12. A compound according to claim 11 in which R$^1$ is hydrogen.

13. A compound according to claim 11 in which n is 4.

14. A compound according to claim 11 in which the radical

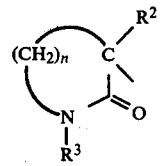

is a hexahydro-1-methyl-2-oxo-azepin-3-yl, 3-ethyl-hexahydro-1-methyl-2-oxo-azepin-3-yl or a 1-propyl-2-oxo-piperid-3-yl radical.

15. A compound according to claim 11 selected from a group consisting of 3-(2-chloro-3-oxocyclohex-1-enyl)-hexahydro-1-methylazepin-2-one, 3-(2-bromo-3-oxocyclohex-1enyl)-hexahydro-1-methylazepin-2-one, 3-(2-bromo-3-oxocyclohex-1-enyl)-3-ethyl-hexahydro-1-methylazepin-2-one, 3-(2-chloro-3-oxocyclohex-1-enyl)-3-ethyl-hexahydro-1-methylazepin-2-one, and 3-(2-bromo-3-oxocyclohex-1-enyl)-1-propyl-2-piperidone.

* * * * *